United States Patent [19]
Hoang

[11] Patent Number: 5,860,972
[45] Date of Patent: Jan. 19, 1999

[54] METHOD OF DETECTION AND DESTRUCTION OF URINARY CALCULI AND SIMILAR STRUCTURES

[75] Inventor: Anh N. Hoang, San Jose, Calif.

[73] Assignee: Xintec Corporation, Oakland, Calif.

[21] Appl. No.: 548,846

[22] Filed: Oct. 26, 1995

[51] Int. Cl.⁶ ................................................ A61N 5/06
[52] U.S. Cl. .................... 606/2.5; 606/127; 606/128; 606/11; 606/12; 606/15; 606/18
[58] Field of Search .......................... 606/2.5, 127, 128, 606/10–12, 15, 17, 18; 600/101; 601/4

[56] References Cited

U.S. PATENT DOCUMENTS 5,269,778  12/1993  Rink et al. ................................ 606/15

OTHER PUBLICATIONS

Article: Use of the Holmium Laser in the Upper Urinary Tract by Bagley et al, Techniques in Urology, vol. 1, No. 1, pp. 25–30 (1995).
Article: Comparison of Holmium and Flashlamp Pumped Dye Lasers for Use in Lithotripsy of Biliary Calculi by Spindel et al, Lasers in Surgery and Medicine 12:482–489 (1992).
Article: Optical Studies of Pulsed–Laser Fragmentation of Biliary Calculi by Teng et al, Applied Physics Bulletin, 42 73–78 (1987).

Technical Data: Hamamatsu Photosensor Modules H5773/H5783/H5784 Series, 1995.

*Primary Examiner*—Lee S. Cohen
*Assistant Examiner*—David M. Ruddy
*Attorney, Agent, or Firm*—Ray K. Shahani, Esq.

[57] ABSTRACT

The present invention relates generally to methods and devices for detecting, destroying and removing urinary calculi and other similar structures anywhere within an animal body, and more specifically to a method for locating such structures, fragmenting and vaporizing them and related detection and control schemes. The method for destruction and detection of urinary stones, calculi and similar structures includes the following steps: (a) providing a laser source suitable for performing laser lithotripsy; (b) initiating transmission of laser energy via a fiber optic laser delivery device so as to impinge upon a urinary stone or other structure and create a sparkle or emission of visible light; (c) transmitting the sparkle or emission of visible light reflected back through the fiber optic laser delivery device to a photomultiplier tube; (d) detecting an amplified signal corresponding to the sparkle or emission of visible light created upon fragmentation of the urinary stones, calculi or other obstruction; (e) creating a control signal for the power supply of the laser source; (f) controlling the laser source so as to continue to transmit laser energy through the fiber optic laser delivery device to a urinary stone or other structure; (g) repeating steps (c) through (f) until no sparkle or visible light emission is detected; and (h) terminating transmission of the laser energy.

7 Claims, 2 Drawing Sheets

METHOD OF DETECTION AND DESTRUCTION OF URINARY CALCULI AND SIMILAR STRUCTURES

FIELD OF THE INVENTION

The present invention relates generally to methods and devices for detecting, fragmenting and removing urinary calculi and other similar structures anywhere within an animal body, and more specifically to a method for locating such structures, fragmenting or otherwise destroying and removing them and related detection and control schemes.

BACKGROUND OF THE INVENTION

Although the first useful lasers were developed in the 1960s, recent advances in laser and fiber optic delivery systems have greatly enhanced the use of this technology in the field of medicine. Today there are numerous types of laser systems designed for operation in a wide range of applications primarily related to surgical and other medical procedures.

Laser fibers are used in different ways, including incision, necrosis or killing of live tissue, excision or removal of tissue and structure, and cauterization of tissue. A very focused beam would provide the greatest amount of control during either operation. Cauterization and necrosis of living tissue is accomplished by coagulation, or more precisely with respect to the laser itself, by photocoagulation of contacted or penetrated tissue. In this process the laser beam causes the proteins in the contacted tissue to heat up rapidly and thermally denature. This essentially kills living tissue and seals blood vessels. The process has been likened to frying an egg. In practice, during an incision procedure cauterization of the incised tissue is likely to occur simultaneously. Thus, laser surgery is often characterized by an absence of bleeding during the surgery.

A common type of laser known as a CO2 laser delivers radiation with a wavelength of 10.64 microns. However, in order to focus or channel the radiated energy produced by a CO2 laser it is necessary to configure sets of mirrors in certain ways. These systems are typically large and expensive. With the mid-1980s FDA approval of the Nd:YAG type laser delivering electromagnetic energy at a wavelength of 1.064 microns, it became possible to generate and focus the laser radiation through a silica core optical fiber. Recently, the Holmium: Yttrium-silver-garnet (Ho:YAG) laser has become an important tool in the hospital and clinic due to it's relatively low cost and wide range of applications suitable for it's use.

Lasers, and in particular Ho:YAG lasers, have been used for a variety of purposes in urology. Such procedures include performing partial or full nephrectomies (removal of one or both of the kidneys), laser-assisted trans-urethral resections of the prostate (a TURP is a procedure required for managing benign prostatic hyperplasia or BPH—a frequent condition caused by swelling of the prostate), treatment of superficial bladder carcinomas or tumors, and other laparascopic procedures.

Numerous modalities exist for the destruction of urinary tract calculi, aside from lasers. These include electrohydraulic probes, ultrasonic probes, electromechanical impactors, and the lithoclast (a compressed air-driven metal pin). Focused shock waves can be delivered from an external source in a procedure known as extracorporeal shock wave lithotripsy or ESWL.

Destruction of gall stones and urinary stones with lasers has been studied as early as 1979. The following is a brief survey of various types of lasers useful for such procedures:

Excimer lasers (xenon, fluoride and xenon chloride) produce shorter wavelength laser radiation. Standard excimer lasers have a pulse duration of 10 nanoseconds which is too short for easy transmission through fibers. Longer pulsed excimer lasers (up to 100 nanoseconds) can be transmitted through optical fibers more easily. Fragmentation of calculi is efficient but one drawback is that both tissue and stone absorb excimer wavelengths strongly, without any beneficial selectivity. The laser is also useful for tissue ablation.

Pulsed dye lasers operate efficiently at a pulse duration of 1 microsecond, which is ideal for stone fragmentation. These lasers emit at wavelengths from the ultraviolet to the red, according to the dye chosen. The maximum differential absorption between stone and ureter tissue occurs at 504 nanometer and this wavelength is, therefore, useful.

Alexandrite lasers are solid-state lasers which emit at 720 nanometer. The pulse duration is typically 10 to 100 nanoseconds, the longer durations more efficiently transmitted. The disadvantage of using the lower durations, with attending high peak pulse power, is that the fiber becomes eroded rapidly during fragmentation of a stone. The longer pulsed alexandrite lasers transmit better but fragmentation of certain calculi is still not highly efficient due to the unfavorable absorption at these wavelengths.

Titanium sapphire lasers are semiconductor lasers, and therefore have the potential to be relatively smaller and more economical than others. They emit at approximately 850 nanometer. Between 3 and 13 microseconds, shorter pulse durations are favored requiring pulse energies of 100 to 200 mJoules to fragment calculi. The action on pale calculi is relatively inefficient and the laser has a variable effect on calculi as the stones shrink and change size and composition during their destruction.

Continuous wave Nd:YAG lasers, though widely used in numerous medical and other applications, should never be used to fragment urinary calculi pulsing the laser will allow fragmentation however. The 100 microsecond laser has been described as having the capability of fragmenting uric acid and gallstones, but not pale calculi. The 10 microsecond Nd:YAG laser has been used at pulse energies of 30 mJoules via 400 micron core fibers to fragment calculi. The high peak power allows fragmentation in spite of poor absorption. At these low-pulse energies, the fiber transmission is feasible. However, the distal end of the fiber is at risk of destruction should it touch the stone. Therefore, solutions include shaping a lens at the distal end of the fiber and placing a metal cap on the end of the fiber which forms a type of shock wave.

The Ho:YAG laser produces light at a wavelength of 2,000 to 2,100 nanometer (2.0 to 2.1 microns), depending upon the precise formulation of the holmium rod, in a pulsed fashion. These wavelengths are well absorbed by water, and thus their use for stone fragmentation is not obvious. Of the devices available, the energy of each pulse and the frequency can be varied. The energy levels typically used are between 0.2 and 2.8 Joules per pulse and the frequency is typically varied between 5 and 20 Hertz. Typical pulse durations are 350 microseconds. The energy produced can be transmitted along suitable silica-based optical fibers, typically ranging in core size between 250 and 750 microns. One drawback of the Ho:YAG laser is that the regimen described has an equally powerful effect on tissue, such as the ureter, and damage can be expected should the laser fiber touch it during delivery.

Endoscopes of various designs are widely used for ureteroscopy. Rigid instruments are generally employed for the distal ureter and may be advanced into the mid- and proxima-ureters in some patients. Actively deflectable, flexible ureteroscopes can be used in the proximal portions of the ureter and the intrarenal collecting system to access most areas. A working channel of at least 2.2 French is recommended for placement of the smaller fibers, such as the 200 micron diameter fiber..

The construction of optical fibers used in surgical procedures is fairly simple. A quartz, plastic or silicone cladding is used to constrain the laser light to the quartz core. Theoretically, only a few of the entering photons are directed straight down the axis of the fiber. Transmission of the radiant beam is possible since the rest of the photons are constrained to the core of the fiber due to internal reflectance by the quartz cladding interface. Very few photons escape the fiber. The technology related to the use of silica core fibers in medical lasers is well known, e.g. B. P. McCann, Photonics Spectra, May 1990, pp 127–136.

SUMMARY OF THE INVENTION

The present invention relates generally to methods and devices for detecting, destroying and removing urinary calculi and other similar structures anywhere within an animal body, and more specifically to a method for locating such structures, fragmenting and vaporizing them and related detection and control schemes. The method for destruction and detection of urinary stones, calculi and similar structures includes the following steps: (a) providing a laser source suitable for performing laser lithotripsy; (b) initiating transmission of laser energy via a fiber optic laser delivery device so as to impinge upon a urinary stone or other structure and create a sparkle or emission of visible light; (c) transmitting the sparkle or emission of visible light reflected back through the fiber optic laser delivery device to a photomultiplier tube; (d) detecting an amplified signal corresponding to the sparkle or emission of visible light created upon fragmentation of the urinary stones, calculi or other obstruction; (e) creating a control signal for the power supply of the laser source; (f) controlling the laser source so as to continue to transmit laser energy through the fiber optic laser delivery device to a urinary stone or other structure; (g) repeating steps (c) through (f) until no sparkle or visible light emission is detected; and (h) terminating transmission of the laser energy. In a preferred embodiment, the method would incorporate the use of a pulsed-type laser source.

In one embodiment, a stone detector system device of the present invention for destroying and detecting the presence of urinary stones, calculi and other obstructions, would comprise a laser source, the laser source suitable for lithotripsy of urinary stones, calculi and other obstructions, and the laser source having a power supply. The system would also comprise a fiber optic laser delivery device, the fiber optic laser delivery device connected to the laser source for transmitting laser energy from the laser source to a urinary stone, calculus or other obstruction and for transmitting sparkle or visible light created by the fragmentation of the urinary stone, calculus or other obstruction from the urinary stone, calculus or other obstruction to a photomultiplier tube (PMT). The PMT is useful for increasing the magnitude of the sparkle or visible light created by the fragmentation of the urinary stone, calculus or other obstruction. A detector would be used for distinguishing between ambient light transmitted from the surface of the urinary stone, calculus or other obstruction and between sparkle or visible light produced by the fragmentation of the urinary stone, calculus or other obstruction. Finally, a controller would be used for controlling the power supply of the laser source, based upon detection by the detector of sparkle or visible light created by the fragmentation of the urinary stone, calculus or other obstruction, to activate the flash lamp of the laser source to generate another pulse of laser energy transmitted to a urinary stone, calculus or other obstruction being removed.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE INVENTION

The present invention relates generally to methods and devices for detecting and removing urinary calculi and other similar structures anywhere within an animal body, and more specifically to a method for locating such structures, fragmenting and vaporizing them and related detection and control schemes.

Following accepted protocol widely disclosed in the medical literature, calculi of all compositions can be fragmented with the holmium laser. When the laser energy is applied through the fiber to a calculus, a small, narrow hole is drilled into the surface of the stone. With continued activation and advancement of the fiber, it can be passed directly through the concretion. Therefore, it is essential to control the depth of the fiber as it passes through the body up to the surface of the stone. To initiate fragmentation it is convenient to set the laser at 0.5 Joules and 5 Hertz. As the effect on the stone is seen, the parameters can be altered as necessary. Higher energy settings may be necessary for harder stones, whereas higher frequency may increase movement of the calculus. Irrigation should be maintained continuously to cool the laser delivery device, the calculus, and the tissue as well as to flush stone debris from the field of view.

Several different methods of fragmentation have been described, including drill and core, fragment and chip, and direct fragmentation. In the first instance, a small hole is drilled directly into the stone, the stone is fragmented from the inside out, and ultimately the outer surface can be fragmented into smaller parts or ablated completely. Care must be taken not to overheat the stone and firing tip of the fiber optic probe, nor should the fiber be advanced too far so as to exit the rear of the stone and cause damage to tissue. Fragmentation and chipping of stones is effected by initiating laser action onto the surface of a stone, creating a crater-like hole or opening, and continuing to chip pieces of the stone away from the crater. As chips are produced they can be fragmented immediately. Direct fragmentation can be employed for the smaller stones and fragments of larger calculi. It can be helpful to apply the fiber along cleavage planes on the surface of the stone. Ultimately, with any procedure employed, pieces of calculus small enough to pass from the ureter spontaneously may be left in place, whereas larger ones may be removed with graspers or baskets.

DEVICE

As discussed, the laser source can be any suitable laser for initiating a flash and for fragmenting stones. The same source can be used or the system can utilize two different laser sources (for example Nd:YAG and Ho:YAG) together in the same procedure, or the laser source can be a modulated waveform output-type laser. In addition to Ho:YAG, other Holmium-type lasers, such as the Ho:YLG or Ho:YLP, may also be used.

Figure 1:
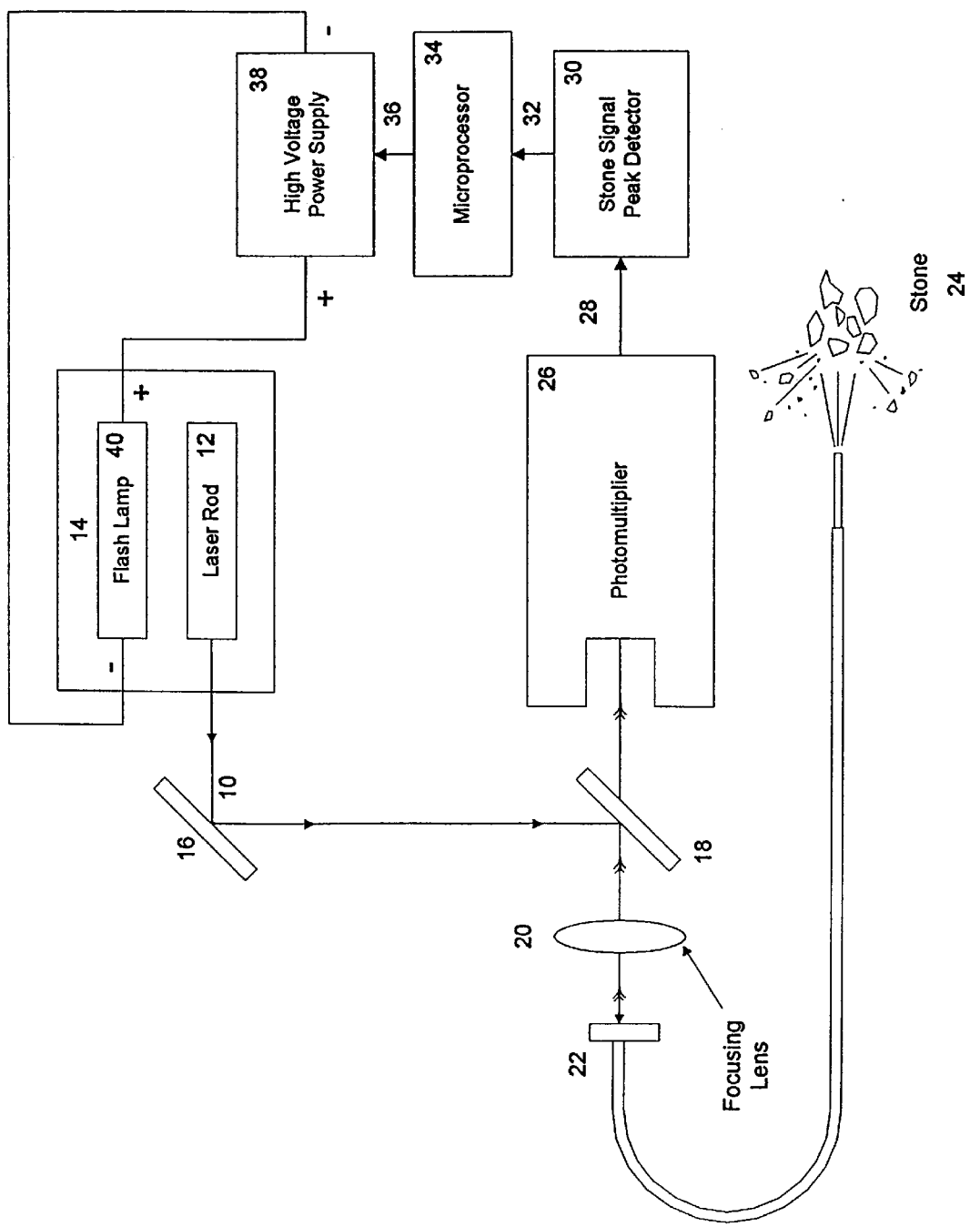
FIG. 1 is a system block diagram of an embodiment of the stone detector system of the present invention.

Any suitable fiber optic probe can be employed, however certain types of probes may be used more efficiently with certain types of lasers. As shown in FIG. 1, interposed between the output of the optical fiber and the stone, an optical gradient type or other type of deflector is placed. The deflector directs a portion of any electromagnetic radiation which is either produced at or bounced off of the surface of the stone. The deflected energy is thereafter detected and amplified by a photomultiplier tube or otherwise.

The photomultiplier tube (or PMT) is a photosensitive device consisting of a photoemissive cathode (photocathode) followed by focusing electrodes, an electron multiplier and an electron collector in a vacuum tube. When light enters the photocathode, the photocathode emits photoelectrons into the vacuum. These photoelectrons are then directed by the focusing electrode voltages towards the electron multiplier where electrons are multiplied by the process of secondary emission. The multiplied electrons are collected by the anode as an output signal.

Because of secondary-emission multiplication, photomultiplier tubes are uniquely sensitive among photosensitive devices currently used to detect radiant energy in the ultraviolet, visible, and near infrared regions. The PMT also features fast time response and low noise. The photocathode of the typical PMT converts energy of incident light into electrons. The conversion efficiency or sensitivity varies with the wavelength of incident light. This relationship between photocathode sensitivity and wavelength is called the spectral response characteristic.

Photoelectrons emitted from a photocathode are accelerated by an electric field so as to strike the first dynode of the particular design of electron multiplier used in the specific PMT, and produce secondary electron emissions. These secondary electrons then impinge upon the next dynode to produce additional secondary electron emissions. Repeating this process over successive dynode stages, a high current amplification is achieved. A very small photoelectric current from the photocathode can be observed as a large output current from the anode of the PMT. Current amplification, or gain, is simply the ratio of the anode output current to the photoelectric current from the photocathode. Gains of 1 million and more are typical.

INITIAL DETECTION

In the absence of an expensive imaging system, locating a stone initially can be difficult, especially in the presence of edematous ureteral mucosa. The present system and device employs a holmium or other suitable type laser. Once the general location has been determined, a single, initial short-duration pulse of laser energy is transmitted. The detector will distinguish between white, brown or yellow calculus deposits and red or black tissue, based upon absorbance of the transmitted light and the remission spectral response. This remission spectra is initially due to reflection of visible or other light back from the stone.

There are several types of calculus which are commonly associated with urinary calculi. These include uric acid, calcium oxalate monohydrate, struvite, cystine and brushite. All of these types of stones are commonly available from testing laboratories throughout the United States, and are commonly divided into three groups. Black stones, commonly known as "pigmented stones", are composed primarily of calcium bilirubinate, are porous and are easy to fragment. White or slightly tanned "cholesterol stones" are composed of cholesterol monohydrate and other minerals and are the hardest to shatter. The third group called "brown" or "mixed" stones have a black and brown surface appearance and are a variable mixture of pigmented and cholesterol stones plus calcium salts, bile acids, bile pigments, fatty acids, proteins, and phospholipids. In general, harder stones tend to shatter or fragment easier than softer stones which must be drilled, chipped, or otherwise worked more extensively over a longer period of time during the operation.

FRAGMENTATION

Once the stone's location is determined, laser activation will result in fragmentation and ablation. A plasma emission is caused by the mechanical stress created in the calculus by the laser. As the stone absorbs laser energy causing heating in a microscopic portion, a plasma is created out of the rapidly expanding electrons. This plasma absorbs more laser energy and generates an acoustic shock wave that overcomes the tensile strength of the stone crystals. It has also been observed that, in addition to the plasma effect, with some softer stones, water which is absorbed into the stone instantaneously vaporizes, expands and results in fragmentation.

With regard to the holmium laser, a pulse of 300 microseconds delivering 0.2 to 1.4 Joules of energy per pulse at a rate of 3–16 Hertz will result in the transmission of 0.11–37.77 total kilojoules. The peak power is the pulse energy divided by the pulse duration in seconds. It is in fact the peak power density that is important in the generation of a plasma and hence of the shock wave. This is the peak power divided by the surface area of the spot size of the laser beam. Since lithotripsy is most commonly achieved by having the laser fiber in contact with the stone, the surface area is essentially the cross section area of the delivery fiber.

A plasma describes the production of an expanding gas bubble, usually due to an electron avalanche. A noise and a flash of white light are characteristic. The expanding gas bubble reaches a peak volume and then collapses with the production of water jets that direct at the stone surface. It is probably the water jet that is most important in effecting the fragmentation. Laser fragmentation is very much less efficient in air than in water, presumably reflecting the importance of the water jets.

A mechanism for the production of this white flash of light was proposed by Teng et al (Optical Studies of Pulsed-laser Fragmentation of Biliary Calculi, *Appl. Phys. B.*, 42, 73–78 (1987)). Laser-induced fragmentation is accompanied by a loud acoustic report, brisk recoil of the laser fiber, and a flash of light. They indicated that this emission of light could be blackbody radiation from hot stone fragments or pyrolysis products, or could be due to the formation of a plasma. While their studies indicated that occasionally a white flash of light was produced without any stone damage occurring, it was apparent that any stone damage was accompanied by the white light emission.

Photographs of fragmentation of the stones immersed in water revealed that fragmentation can occur well below the surface of the stone, suggesting that the process is not simply a surface phenomenon such as surface etching. Fragmentation of laser stones was about 4 times as efficient under water than in air. Therefore, as contemplated by others, the picture of plasma production involved the vaporization of some of the target material, with subsequent absorption in the vaporized material, leading to plasma formation. The plasma subsequently becomes the primary absorber, shielding the target optically, and forming an acoustic impulse that mechanically couples to the target.

A likely sequence of events begins with the absorption of laser energy by the stone with consequent heating. Some microscopic particles may be ablated or individual molecules desorbed to form absorption sites in the region in front the stone. When a sufficiently high temperature is reached by the stone surface or particles or molecules between the stone and the fiber, a plasma is formed. This plasma absorbs the laser light and prevents further delivery of light to the stone. The plasma expands as it absorbs laser energy. The expansion of the plasma is confined by the quartz fiber and surrounding water when the stones are immersed. This mechanical confinement leads to the formation of a acoustic transient which leads to stone fracture. This sequence of plasma-initiated events is necessary for stone material removal; the associated visible flash, acoustic report, and palpable fiber recoil can in fact help guide laser dosimetry during treatment.

CONTROL

Although the observation of a flash of white light occurring upon the fragmentation of calculi has been made in the past, this remission spectra has never been used in a system as a control indicator. Since this flash is only created at the time the stone fragments, it's presence is an excellent indicator of the extent of fragmentation of the individual stone being removed. Utilizing the detector comprising a photomultiplier tube or other photoamplifier, the "sparkle" or flash of white light can be detected. Today's PMT technology makes possible the detection of very low levels of light. This affords the surgeon an extremely accurate indication of the immediate effect of the laser energy, the absence of the plasma light for any brief period of time indicating no further fragmentation. Thereafter, the surgeon will terminate laser activation and transmission. This novel fragmentation and detection system will prevent overheating of a stone or fiber firing tip as well as provide a definite and visible indicator that fragmentation is complete. This will prevent tissue damage which is one of the leading causes of post-operative morbidity in patients undergoing laser lithotripsy.

With respect to FIG. 1, laser energy 10 from the rod of lasing material or gain material 12 of a typical laser 14 is directed, by a set of diffraction gratings or mirrors 16 and 18 through a focusing lens 20 and into the end of a fiber optic laser delivery device 22. A pulsed laser is preferred. The diffraction gratings or mirrors are mounted, in a preferred embodiment, at roughly 45 degrees to the central axis of the laser output. These mirrors are made to reflect approximately 99% of the incident infrared radiation but will allow the transmission of as much as 85% of any visible light (300–700 nanometer). It will be obvious to one skilled in the art that a variety of different configurations of mirrors, diffraction gratings, refraction gratings or other optical devices with selective optical properties can be used and will be considered equivalent to the preferred embodiment. For simplicity, the term "mirrors" will be understood to include optical devices exhibiting and allowing reflection and/or transmittance of incident laser and visible and other radiation.

Once the laser energy enters the end of the fiber optic laser delivery device, it will be delivered out the transmitting end and will impinge upon a stone to be fragmented. As the laser energy creates a plasma in front of the tip of the fiber, an air bubble will be created. While the air bubble initially gets larger, it eventually will collapse, and multiple jets of water will immediately seek to fill the void created by the collapse of the bubble. These multiple jets of water create strong forces which collide together and crack the stone 24.

As the stone fractures, the observed flash of white light has a high intensity. This flash of light is in sync (i.e. is produced essentially simultaneously) with the transmission of the laser pulse. This flash of visible light is partially reflected back along the optical fiber and is transmitted through the focusing lens by the fiber. However, rather than being reflected by mirror 18, the visible light is transmitted through the mirror or other optical device and directed to photomultiplier tube 26. The PMT will not detect the infrared beam but will, rather, only amplify the visible light of the sparkle. The output 28 from the PMT is directed to a stone signal peak detector 30. This stone detector can distinguish and ascertain the differences between a signal produced by the dark level, a signal produced by the ambient light reflected back from the stone, and the sparkle light from the fragmented stone. It will be understood by those skilled in the art that the PMT of the preferred embodiment could be replaced with and will be considered equivalent to other devices capable of detecting a flash or other emissive response such as that produced by photostimulation of the urinary stone or similar structure. This device will be referred to hereafter as a photomultiplier tube and will be construed as including other devices serving the same purpose as amplifying an emissive response so as to produce a useful signal with greater resolution and manipulability. The amplified signal can be used to generate a control signal to the laser power source in any of numerous ways, including processing of the amplified signal via solid-state devices, etc.

When the detector detects the sparkle of the stone, the detector will send a detection signal 32 to a microprocessor 34. The detection signal will instruct the microprocessor to send a control signal 36 to the high voltage power supply 38 of the laser. This power supply is then activated to stimulate a flash lamp 40 which in turn will create another pulse of laser energy delivered from the laser rod through the fiber optic laser delivery device to the stone.

Figure 2:
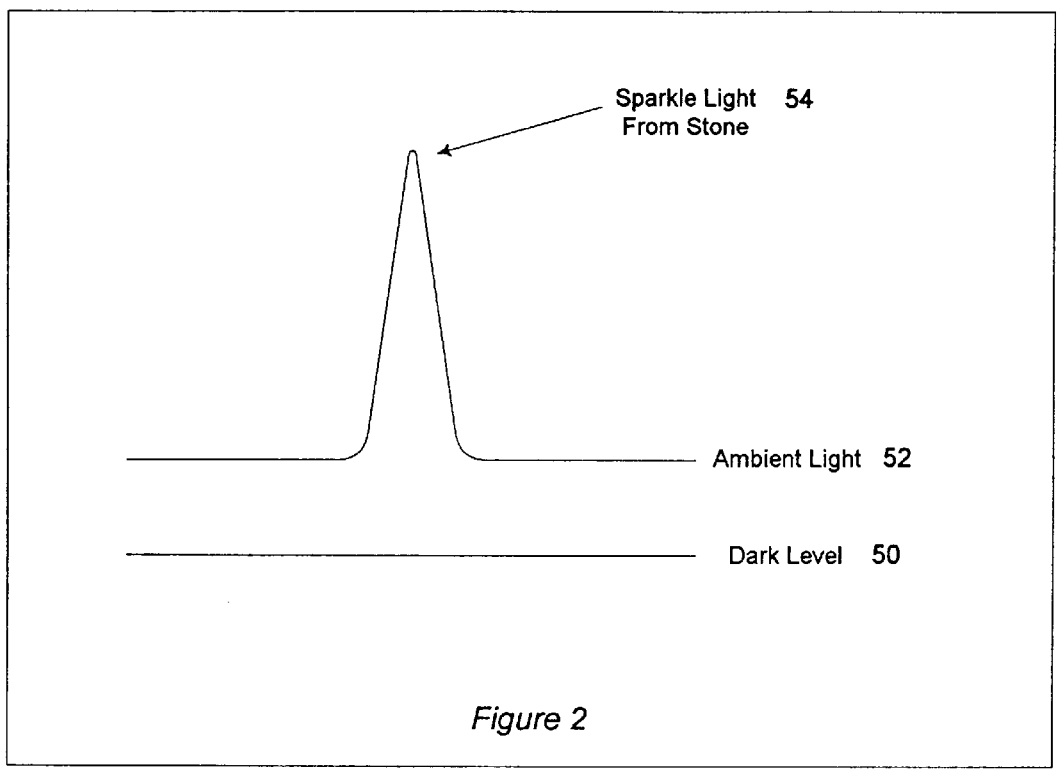
FIG. 2 is a schematic diagram of the signals generated by the stone signal detector.

FIG. 2 is a schematic diagram of the signals generated by the stone signal detector. As mentioned above, the dark level signal 50 would correspond to a signal received and amplified by the PMT corresponding to no ambient light shining on the PMT. The ambient light level 52 corresponds to the ambient light seen by (transmitted by) the end of the fiber optic laser delivery device in the absence of the discrete sparkle or flash of visible light produced upon fragmentation of a stone. The "sparkle light from stone" peak 54 is the visual representation of the amplitude of the light signal transmitted by the fiber optic laser delivery device which would be observable immediately preceding the fragmentation of a stone. This sharp peak could be easily detected and distinguished over a general baseline (such as the ambient light threshold) and is indication that fragmentation has just occurred. In some embodiments, the stone signal detector could be a type of analog to digital convertor—when the analog signal peak is detected the detector could be a signal to the controller of the laser source to instruct the laser source to fire another pulse of laser energy at the stone just fragmented to continue or complete fragmentation of that particular stone.

This stepwise procedure will continue as long as a stone is detected. An initial laser pulse will result in the sparkle of a stone during fragmentation. This sparkle is observed and transmitted to a photomultiplier tube. The signal is multiplied and ultimately is detected by the stone detector based upon the difference in intensity between the observed sparkle and any ambient light or other baseline value. The signal from the detector is processed by a microprocessor and is used to activate the power supply of the laser to induce stimulation and emission from the laser rod to create another pulse of laser energy.

The cycle will repeat as long as for each pulse of laser energy, a corresponding flash of white light is observed. However, if no sparkle is detected, the power supply of the laser will be prevented from activating the flash lamp and stimulating the laser rod. In this manner, there is no possibility that the laser energy will impinge upon non-calculus material (for example surrounding tissue) for a duration greater than one pulse in duration. This safety feature will virtually eliminate the post-operative morbidity and other complications caused by the accidental laser impingement of otherwise healthy, normal tissue not to be removed with the urinary obstruction.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

I claim:

1. A method of destruction and detection of urinary calculi, including the following steps:

(a) Providing a laser source suitable for performing laser lithotripsy;
   (b) Initiating transmission of laser energy from the laser source via a fiber optic laser delivery device so as to impinge upon urinary calculi and create a sparkle or emission of visible light;
   (c) Transmitting the sparkle or emission of visible light reflected back through the fiber optic laser delivery device to a photomultiplier tube;
   (d) Detecting an amplified signal from the photomultiplier tube corresponding to the sparkle or emission of visible light created upon fragmentation of the urinary calculi;
   (e) Creating a control signal for the power supply of the laser source;
   (f) Controlling the laser source so as to continue to transmit laser energy through the fiber optic laser delivery device to the urinary calculi;
   (g) Repeating steps (c) through (f) until no sparkle or visible light emission is detected; and
   (h) Terminating transmission of the laser energy.

2. The method of claim 1 wherein the laser source used is a pulsed laser source.

3. The method of claim 1 wherein the laser source is a Holmium-type laser.

4. The method of claim 1 wherein the laser source is a Ho:YAG laser.

5. A method of detection and destruction of urinary calculi comprising the steps of providing a laser source powered by a microprocessor-based high voltage power supply and a fiber optic laser delivery device, providing a set of optical devices to selectively focus, transmit and reflect radiation, providing a photomultiplier tube, providing a stone signal detector and signal microprocessor, initiating laser energy transmission from the laser source and delivering an initial pulse of laser radiation via the set of optical devices to the urinary calculi thereby causing to be emitted a flash or sparkle of visible light, detecting the flash or sparkle of visible light by transmitting the flash or sparkle of visible light to the photomultiplier tube and amplifying the flash or sparkle of visible light, transmitting the detected flash or sparkle of visible light to the stone signal detector, generating a control signal from a microprocessor based on input from the stone signal detector, and controlling the high voltage power supply, whereby whenever laser energy transmission is initiated, an initial pulse of laser energy will detect the presence of the urinary calculi by detecting a flash or sparkle of visible light from the urinary calculi, flash or sparkle of visible light being amplified and converted via the stone signal detector to the signal an input to the microprocessor for controlling the high voltage power supply of the laser source, and continuing to deliver pulses of laser energy to the urinary calculi as long as the flash or sparkle of visible light is detected, and continuing until the urinary calculi has been fragmented completely, which point is indicated by the failure to produce the flash or sparkle of visible light.

6. The method of claim 5 wherein the laser source is a Holmium-type laser.

7. The method of claim 5 wherein the laser source is a Ho:YAG laser.

* * * * *